(12) United States Patent
Andrus

(10) Patent No.: US 10,292,700 B2
(45) Date of Patent: May 21, 2019

(54) ANCHOR OR STAPLE WITH BARBS

(71) Applicant: HeartWare, Inc., Miami Lakes, FL (US)

(72) Inventor: Lance Lynn Andrus, Southborough, MA (US)

(73) Assignee: HeartWare, Inc., Miami Lakes, FL (US)

( * ) Notice: Subject to any disclaimer, the term of this patent is extended or adjusted under 35 U.S.C. 154(b) by 123 days.

(21) Appl. No.: 15/186,889

(22) Filed: Jun. 20, 2016

(65) Prior Publication Data

US 2016/0374674 A1     Dec. 29, 2016

Related U.S. Application Data

(60) Provisional application No. 62/183,497, filed on Jun. 23, 2015.

(51) Int. Cl.
| | |
|---|---|
| *A61B 17/06* | (2006.01) |
| *A61B 17/064* | (2006.01) |
| *A61B 17/04* | (2006.01) |
| *A61B 17/00* | (2006.01) |
| *A61M 1/10* | (2006.01) |
| *A61M 1/12* | (2006.01) |

(52) U.S. Cl.
CPC ........ *A61B 17/0644* (2013.01); *A61B 17/064* (2013.01); *A61B 2017/00243* (2013.01); *A61B 2017/043* (2013.01); *A61B 2017/0435* (2013.01); *A61B 2017/0464* (2013.01); *A61B 2017/0647* (2013.01); *A61M 1/101* (2013.01); *A61M 1/1008* (2014.02); *A61M 1/122* (2014.02)

(58) Field of Classification Search
CPC .............. A61B 17/064; A61B 17/0644; A61B 17/844; A61B 2017/0435; A61B 2017/0437; A61B 2017/0647; A61B 2017/8655

See application file for complete search history.

(56) References Cited

U.S. PATENT DOCUMENTS

| | | | |
|---|---|---|---|
| 4,799,495 A * | 1/1989 | Hawkins ............ | A61B 17/3403 600/567 |
| 5,141,520 A | 8/1992 | Goble et al. | |
| 5,417,712 A * | 5/1995 | Whittaker .......... | A61B 17/0401 606/232 |
| 5,472,452 A | 12/1995 | Trott | |

(Continued)

*Primary Examiner* — Alexander J Orkin
(74) *Attorney, Agent, or Firm* — Christopher & Weisberg, P.A.

(57) ABSTRACT

A tissue anchor includes an elongated body having a proximal end and a distal end, and a barb mounted to the elongated body adjacent the proximal end for movement between a retracted position and an extended position in which the barb projects outwardly from the elongated body. An anchoring system includes an implantable device with a tissue contacting surface facing in a proximal direction, the tissue anchor having its distal end engageable with the implantable device and its proximal end adapted to project proximally beyond the tissue contacting surface to grip a living tissue, and a second resilient element that is mounted between the distal end of the anchor and the implantable device, the second resilient element being adapted to bias the anchor distally relative to the implantable device. Tooling and methods of insertion and removal are provided.

10 Claims, 10 Drawing Sheets

(56) References Cited

U.S. PATENT DOCUMENTS

| | | |
|---|---|---|
| 5,702,215 A | 12/1997 | Li |
| 5,944,750 A * | 8/1999 | Tanner ................. A61B 17/068 606/108 |
| 5,997,556 A | 12/1999 | Tanner |
| 6,030,402 A * | 2/2000 | Thompson ......... A61B 17/3494 606/105 |
| 6,363,938 B2 * | 4/2002 | Saadat ................. A61F 2/2493 128/898 |
| 6,506,190 B1 * | 1/2003 | Walshe ............. A61B 17/0401 606/139 |
| 6,981,983 B1 * | 1/2006 | Rosenblatt ........ A61B 17/0401 128/898 |
| 7,771,443 B2 * | 8/2010 | Copa ..................... A61B 17/11 606/153 |
| 8,029,535 B2 | 10/2011 | Ortiz et al. |
| 8,034,080 B2 * | 10/2011 | Malandain ........... A61B 17/025 606/249 |
| 8,114,131 B2 * | 2/2012 | Kohm ................ A61B 17/7065 606/248 |
| 8,142,479 B2 * | 3/2012 | Hess .................. A61B 17/7065 606/248 |
| 8,353,921 B2 | 1/2013 | Schaller et al. |
| 8,926,697 B2 | 1/2015 | Gross et al. |
| 8,942,829 B2 | 1/2015 | Rothstein et al. |
| 2004/0002735 A1 * | 1/2004 | Lizardi ............... A61B 17/0401 606/232 |
| 2004/0078054 A1 * | 4/2004 | Biggs ............... A61B 17/00234 606/232 |
| 2004/0171905 A1 | 9/2004 | Yu et al. |
| 2005/0038370 A1 * | 2/2005 | Kuth ...................... A61B 1/041 602/78 |
| 2007/0134993 A1 | 6/2007 | Tamez et al. |
| 2009/0125071 A1 * | 5/2009 | Skinlo ................ A61B 17/0401 606/300 |
| 2010/0023055 A1 | 1/2010 | Rousseau |
| 2010/0023117 A1 | 1/2010 | Yoganathan et al. |
| 2010/0160935 A1 * | 6/2010 | Karpiel ................ A61B 17/083 606/142 |
| 2011/0082538 A1 | 4/2011 | Dahlgren et al. |
| 2012/0157761 A1 * | 6/2012 | Crank ................... A61F 2/0045 600/37 |
| 2012/0245606 A1 * | 9/2012 | Goldberg ............... A61B 17/11 606/153 |
| 2014/0100651 A1 * | 4/2014 | Kheradvar ......... A61B 17/0643 623/2.1 |
| 2014/0324069 A1 | 10/2014 | Gerber et al. |
| 2015/0112120 A1 | 4/2015 | Andrus |

* cited by examiner

ANCHOR OR STAPLE WITH BARBS

CROSS-REFERENCE TO RELATED APPLICATION

The present application claims the benefit of the filing date of U.S. Provisional Patent Application No. 62/183,497 filed Jun. 23, 2015, the disclosure of which is hereby incorporated herein by reference.

BACKGROUND OF THE INVENTION

The present invention relates to components and methods used for attaching implantable devices to muscular tissue. An exemplary use for the present invention would be to affix a ventricular assist device, and associated elements (together, a "VAD"), to the heart of a living subject.

The heart is sometimes incapable of providing sufficient pumping capacity to meet the needs of the body. The effects of this inadequacy can be alleviated by providing a VAD that includes one or more mechanical pumps that supplement the pumping action of the heart. Each pump, like all other elements of the VAD, is preferably implantable in the living subject to supplement or replace the pumping action of the heart for an extended period of time. In some cases, the subject may have a VAD implanted for years while awaiting a suitable donor for a heart transplant.

A VAD usually has an inlet connected to the left ventricle. Most VADs have an outlet tube which is connected to the aorta. During operation, the VAD assists the heart to pump blood from the left ventricle to the aorta. In a typical case, the VAD is connected to the heart through the use of a mounting ring, as disclosed in U.S. Published Patent Application Nos. 2004/0171905 and 2007/0134993, the disclosures of which are hereby incorporated herein by reference.

In many cases, the mounting ring is fastened to the exterior of the heart. Each mounting ring typically has a hole that is placed over a corresponding hole formed in a wall of the heart. The VAD may then be secured to the mounting ring so that the VAD inlet extends into heart through respective holes in the mounting ring and the wall of the heart.

Sutures are commonly used to anchor the mounting ring to the heart. The time required to suture the ring to the heart adds to the time that a patient must be kept under anesthesia. Because many patients requiring VADs are generally frail, this additional time requirement is a significant drawback. Other types of anchors have also been contemplated; including those disclosed U.S. application Ser. No. 14/519,850, the disclosure of which is hereby incorporated herein by reference. Further improvements are required.

Despite their intended long life, a VAD, or elements of the VAD, may need to be replaced or upgraded before the patient is able to receive a donor heart. This may require the mounting ring, for example, to be detached from the heart. Some known anchoring means, such as sutures, can also be time-consuming or difficult to remove. This yet additional time requirement may also increase the health risks associated with the removal procedure. Further improvements are required to resolve these issues as well.

BRIEF SUMMARY OF THE INVENTION

A first aspect of the present invention is a tissue anchor including an elongated body having a proximal end and a distal end, and a barb mounted to the elongated body adjacent the proximal end for movement between a retracted position and an extended position in which the barb projects outwardly from the elongated body.

In accordance with other embodiments of the first aspect, the proximal end may have a tissue penetrating tip. The elongated body may have an opening adjacent the proximal end and a pivot end of the barb may be pivotally mounted to the body within the opening. The entire barb may be disposed through the opening and within the elongated body when in the retracted position. A first resilient element may be connected between the elongated body and the barb to bias the barb toward the extended position. The first resilient element may be housed within the elongated body proximal to the pivot end of the barb. The barb may be movable into the retracted position through the application of a force to the pivot end, thereby compressing the first resilient element. The elongated body may have a bore extending from the pivot end to an opening in the distal end, the bore being sized to receive a tool adapted to apply the force to the pivot end through the bore.

A second aspect of the present invention is a method of anchoring an implantable device to a living tissue using a tissue anchor, the tissue anchor including an elongated body having a proximal end and a distal end, and a barb mounted to the elongated body adjacent the proximal end for movement between a retracted position and an extended position in which the barb projects outwardly from the elongated body. The method includes the steps of placing a proximal surface of the implantable device adjacent the living tissue, driving the tissue anchor into the living tissue through an opening in the implantable device, and moving the barb into the extended position so as to grip the living tissue and hold the proximal surface of the implantable device adjacent the living tissue.

In accordance with other embodiments of the second aspect, the method may further include the step of holding the implantable device in a fixed position relative to the living tissue before moving the barb into the extended position. The method may further include the step of compressing a second resilient element seated between a distal end of the tissue anchor and a surface of the implantable device as the barb is moved into the extended position. The barb may have a barb length, and the second resilient element may have a travel length equal to about two thirds of the barb length. The method may further include the step of decompressing the second resilient element so as to sink the barb into the living tissue.

A third aspect of the present invention is a method of removing an implantable device and a tissue anchor from a living tissue, the tissue anchor including an elongated body having a proximal end and a distal end, and a barb mounted to the elongated body adjacent the proximal end for movement between a retracted position and an extended position in which the barb projects outwardly from the elongated body. The method includes the steps of holding the implantable device in a fixed position relative to the living tissue, moving the barb into the retracted position, and removing the tissue anchor and the device from the living tissue.

A fourth aspect of the present invention is a method of using an implantable device with a tissue anchor, the tissue anchor including an elongated body having a proximal end and a distal end, and a barb mounted to the elongated body adjacent the proximal end for movement between a retracted position and an extended position in which the barb projects outwardly from the elongated body. The method includes the steps of driving the tissue anchor through an opening in the implantable device, and moving the barb into the extended position.

In accordance with other embodiments of the fourth aspect, the method may further include the step of holding the implantable device in a fixed position before moving the barb into the extended position. The method may further include the step of compressing a second resilient element seated between a distal end of the tissue anchor and a surface of the implantable device as the barb is moved into the extended position. The barb may have a barb length, and the second resilient element may have a travel length equal to about two thirds of the barb length. The method may further include the step of decompressing the second resilient element.

A fifth aspect of the present invention is a method of removing a tissue anchor from an implantable device, the tissue anchor including an elongated body having a proximal end and a distal end, and a barb mounted to the elongated body adjacent the proximal end for movement between a retracted position and an extended position in which the barb projects outwardly from the elongated body. The method includes the steps of holding the implantable device in a fixed position, moving the barb into the retracted position, and removing the tissue anchor from the device.

A sixth aspect of the present invention is an anchoring system including an implantable device with a tissue contacting surface facing in a proximal direction, a tissue anchor with an elongated body having a distal end engageable with the implantable device and a proximal end adapted to project proximally beyond the tissue contacting surface to grip a living tissue, and a second resilient element that is mounted between the distal end of the anchor and the implantable device, the second resilient element being adapted to bias the anchor distally relative to the implantable device.

In accordance with other embodiments of the sixth aspect, the second resilient element may be seated within an opening in the implantable device. The second resilient element may be a spring. The second resilient element may be a hollow annulus. The tissue anchor may include a securement element disposed adjacent the proximal end of the elongated body that is movable between a retracted position and an extended position in which the securement element projects outwardly from the elongated body. The securement element may be a barb. The elongated body may have an opening adjacent the distal end and a pivot end of the barb may be pivotally mounted to the elongated body within the opening. A first resilient element may be connected between the elongated body and the barb to bias the barb toward the extended position. The first resilient element may be housed within the elongated body proximal to the pivot end of the barb and compressed by the pivot end when the barb is moved into the retracted position. The barb may have a barb length, and wherein the second resilient element may have a travel length equal to about two thirds of the barb length.

A seventh aspect of the present invention is a tool for use with an implantable device and a tissue anchor adapted to secure the device to a living tissue, the tool including a tool body that extends along a tool axis between a distal end and a proximal end, a securing feature adapted to removably secure the implantable device to the proximal end of the tool body, an elongated rod with a driving portion that is engageable with the tissue anchor, and an actuator operable to drive the anchor, when engaged with the driving portion of the rod, into the tissue through an opening in the device.

In accordance with other embodiments of the seventh aspect, the proximal end of the tool body may have a first flange and the securing feature may include a second flange that is moveable along the tool axis so as to secure a portion of the implantable device between the first and second flanges. The second flange may have at least one nub extending away from the tool axis, each of the at least one nubs being sized for receipt within a corresponding notch in the device. The driving portion of the rod may include a gripping portion adapted to releasably engage a portion of the anchor. The gripping portion may be a cap that is mounted to the rod and sized to releasably engage a head of the anchor, the cap being adapted to release the head when the anchor is driven into the anchor opening. The driving portion of the rod may be adapted to move a barb of the anchor into a retracted position thereof when the cap is releasably engaged with the head of the anchor. The tool may further include a first resilient element mounted in the anchor so as to bias the barb towards the extended position. The tool may further include a second resilient element mounted to the device so as to bias the anchor distally away from the device. The actuator may be a knob attached to a driveshaft that is threadably connected to a plunger within the tool body, the plunger being configured for translational movement along the tool axis when the knob is rotated.

An eighth aspect of the present invention is a method of anchoring an implantable device to living tissue using a tool, the tool for use with the implantable device and a tissue anchor adapted to secure the device to a living tissue, the tool including a tool body that extends along a tool axis between a distal end and a proximal end, a securing feature adapted to removably secure the implantable device to the proximal end of the tool body, an elongated rod with a driving portion that is engageable with the tissue anchor, and an actuator operable to drive the anchor, when engaged with the driving portion of the rod, into the tissue through an opening in the device. The method includes the steps of securing the device to the proximal end of the tool body, engaging the driving portion of the elongated rod with the tissue anchor, operating the actuator to engage the anchor with the tissue through an opening in the device, unsecuring the device from the proximal end of the tool body, and moving the tool away from the tissue.

In accordance with other embodiments of the eighth aspect, the actuator may be a knob attached to a driveshaft that is threadably connected to a plunger within the tool body, the plunger being configured for translational movement along the tool axis when the knob is rotated, and the step of operating the actuator may include rotating the knob to advance the anchor proximally until the anchor engages the tissue through the opening.

A ninth aspect of the present invention is a method of removing an implantable device from living tissue using a tool, the tool for use with the implantable device and a tissue anchor adapted to secure the device to a living tissue, the tool including a tool body that extends along a tool axis between a distal end and a proximal end, a securing feature adapted to removably secure the implantable device to the proximal end of the tool body, an elongated rod with a driving portion that is engageable with the tissue anchor, and an actuator operable to drive the anchor, when engaged with the driving portion of the rod, into the tissue through an opening in the device. The method includes the steps of securing the device to the proximal end of the tool body, engaging the driving portion of the elongated rod with the tissue anchor, operating the actuator to disengage the anchor from the tissue, and moving the device and the anchor away from the tissue.

In accordance with other embodiments of the ninth aspect, the actuator may be a knob attached to a driveshaft that is threadably connected to a plunger within the tool body, the plunger being configured for translational movement along the tool axis when the knob is rotated, and the step of operating the actuator may include rotating the knob to advance the anchor distally until the anchor is disengaged from the tissue.

A tenth aspect of the present invention is a method of using an implantable device with a tool, the tool for use with the implantable device and a tissue anchor adapted to secure the device to a living tissue, the tool including a tool body that extends along a tool axis between a distal end and a proximal end, a securing feature adapted to removably secure the implantable device to the proximal end of the tool body, an elongated rod with a driving portion that is engageable with the tissue anchor, and an actuator operable to drive the anchor, when engaged with the driving portion of the rod, into the tissue through an opening in the device. The method includes the steps of securing the device to the proximal end of the tool body, engaging the driving portion of the elongated rod with the tissue anchor, operating the actuator to move the anchor through an opening in the device, unsecuring the device from the proximal end of the tool body, and moving the tool away from the device.

In accordance with other embodiments of the tenth aspect, the actuator may be a knob attached to a driveshaft that is threadably connected to a plunger within the tool body, the plunger being configured for translational movement along the tool axis when the knob is rotated, and the step of operating the actuator may include rotating the knob to advance the anchor proximally through the opening.

An eleventh aspect of the present invention is a method of using an implantable device with a tool, the tool for use with the implantable device and a tissue anchor adapted to secure the device to a living tissue, the tool including a tool body that extends along a tool axis between a distal end and a proximal end, a securing feature adapted to removably secure the implantable device to the proximal end of the tool body, an elongated rod with a driving portion that is engageable with the tissue anchor, and an actuator operable to drive the anchor, when engaged with the driving portion of the rod, into the tissue through an opening in the device. The method includes the steps of securing the device to the proximal end of the tool body, engaging the driving portion of the elongated rod with the tissue anchor, and operating the actuator to move the anchor.

In accordance with other embodiments of the eleventh aspect, the actuator may be a knob attached to a driveshaft that is threadably connected to a plunger within the tool body, the plunger being configured for translational movement along the tool axis when the knob is rotated, and the step of operating the actuator may include rotating the knob to advance the anchor distally.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

The present invention is described below with reference to specific embodiments of a tissue anchor or staple with barbs and associated methods, systems, tools, and other inventions. It is to be understood that the concepts and novelty underlying each embodiment could be utilized for any type of medical procedure requiring attachment of one or more devices to living tissue. Moreover, although described in connection with living tissue, it is contemplated that the present invention may be used for attaching any device to variety of surfaces.

As used herein, the term "proximal" means towards to a living tissue and "distal" means away from living tissue. In the case of the heart, each of the proximal and distal directions has been labeled with a respected "P" and "D" arrow in certain drawings. Embodiments of the present invention are thus described as having a proximal-distal axis with respect to the orientation of the invention in an operative condition. These descriptors are provided for convenience and not intended to limit the present invention to a particular orientation or physical location.

Figure 1:
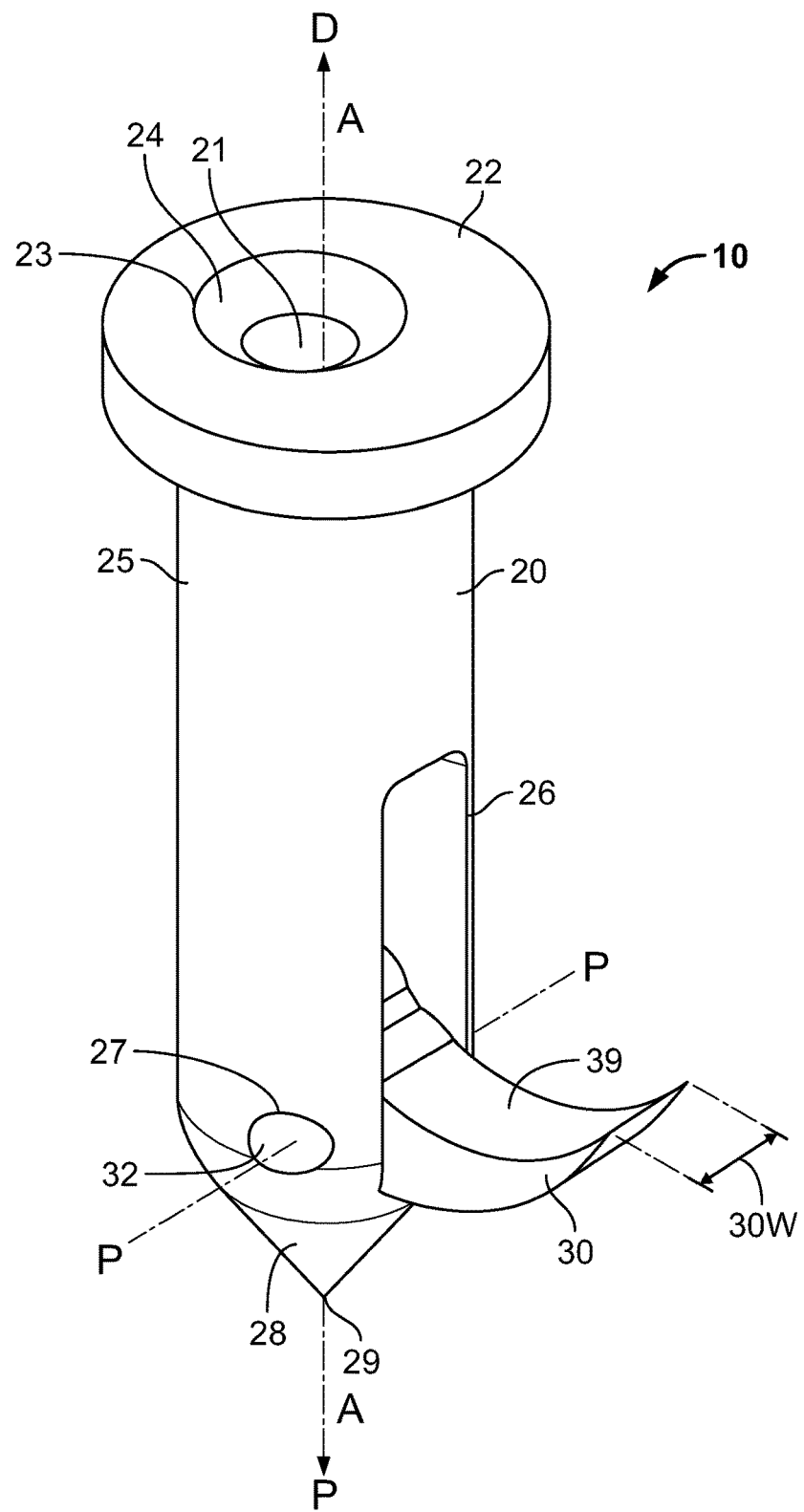
FIG. 1 is a front perspective view of a tissue anchor or staple in accordance with one embodiment of the present invention.

One embodiment of the present invention includes a tissue anchor or staple adapted to secure an implantable device to a living tissue, such as the human heart. An exemplary tissue anchor 10 is illustrated in FIG. 1 as having an elongated body 20 with a distal end or head 22 and a proximal end or tip 28. A barb 30 is mounted to body 20 adjacent tip 28. FIG. 1 also depicts an anchor axis A-A extending longitudinally in a proximal-distal direction through anchor 10. Head 22 and tip 28 are disposed oppositely along axis A-A. A bore 21 extends partially through body 20, between head 22 and the vicinity of tip 28, in a direction parallel to axis A-A. As described below, a portion of a tool 70 is inserted through bore 21 to implant anchor 10.

Figure 3A:
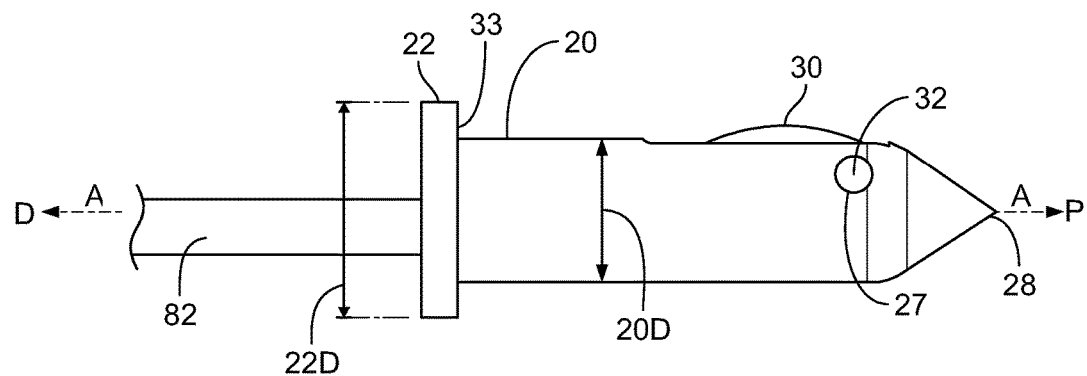
FIG. 3A is a side elevation view of the tissue anchor shown in FIG. 1 with a barb in a retracted position.

Distal head 22 of elongated body 20 is preferably adapted to engage a surface of an implantable device, such as device 50 described below. For example, head 22 is depicted in FIG. 3A as having an outer or head diameter 22D that is greater than an outer or body diameter 20D of elongated body 20. This difference provides tissue anchor 10 with the "T" shaped profile of FIG. 3A, wherein head 22 extends outwardly from body 20 to define a proximal surface 33 of anchor 10. A bore opening 24 extends through distal head 22 to be in communication with bore 21. Preferably, as in FIG. 3B, bore opening 24 has a bore opening diameter 24D that is larger than a bore diameter 21D of bore 21 so as to define a chamfered entry 23 (FIG. 1) of bore opening 24 that is adapted to guide a portion of a tool 70 into bore 21.

Body 20 of FIG. 1 has an exterior surface 25 with a barb opening 26. Exterior surface 25 is depicted as cylindrical with a smooth finish. Exemplary barb opening 26 of FIG. 1 is in communication with bore 21. Preferably, barb opening 26 is disposed adjacent proximal tip 28 and adapted to receive at least one barb 30 therein. For example, barb opening 26 is also in communication with a pin hole 27 that extends through at least a portion of body 20 along a pin hole axis P-P that is transverse with axis A-A. Barb opening 26 of FIG. 3B also has an internal cavity 41 that is in communication with bore 21. As noted below, at least a portion of internal cavity 41 is preferably intersected by anchor axis A-A.

Figure 6:
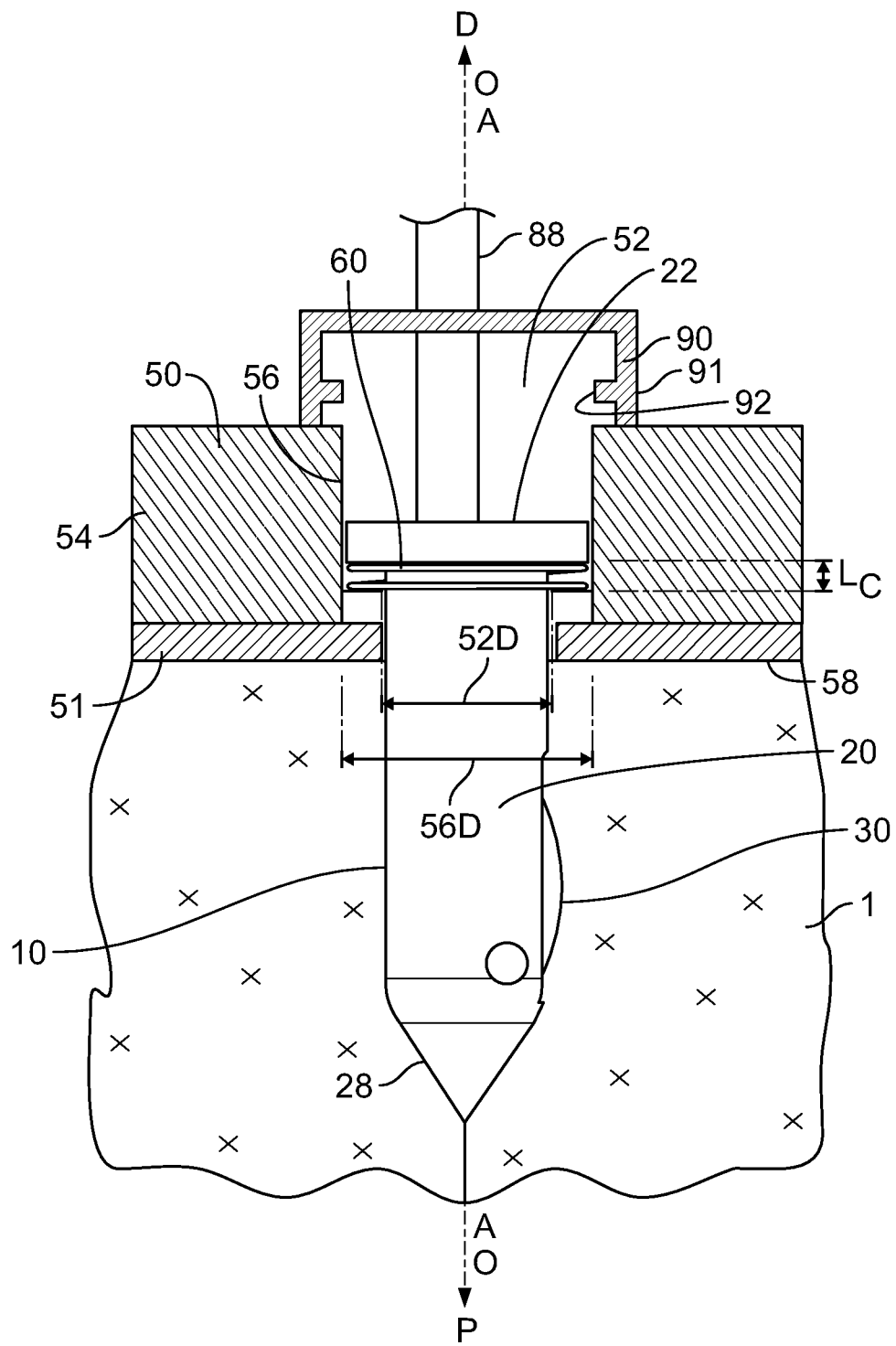
FIGS. 6 and 7 are front elevation views of the tissue anchor shown in FIG. 1 disposed within the device shown in FIG. 2.
Figure 7:
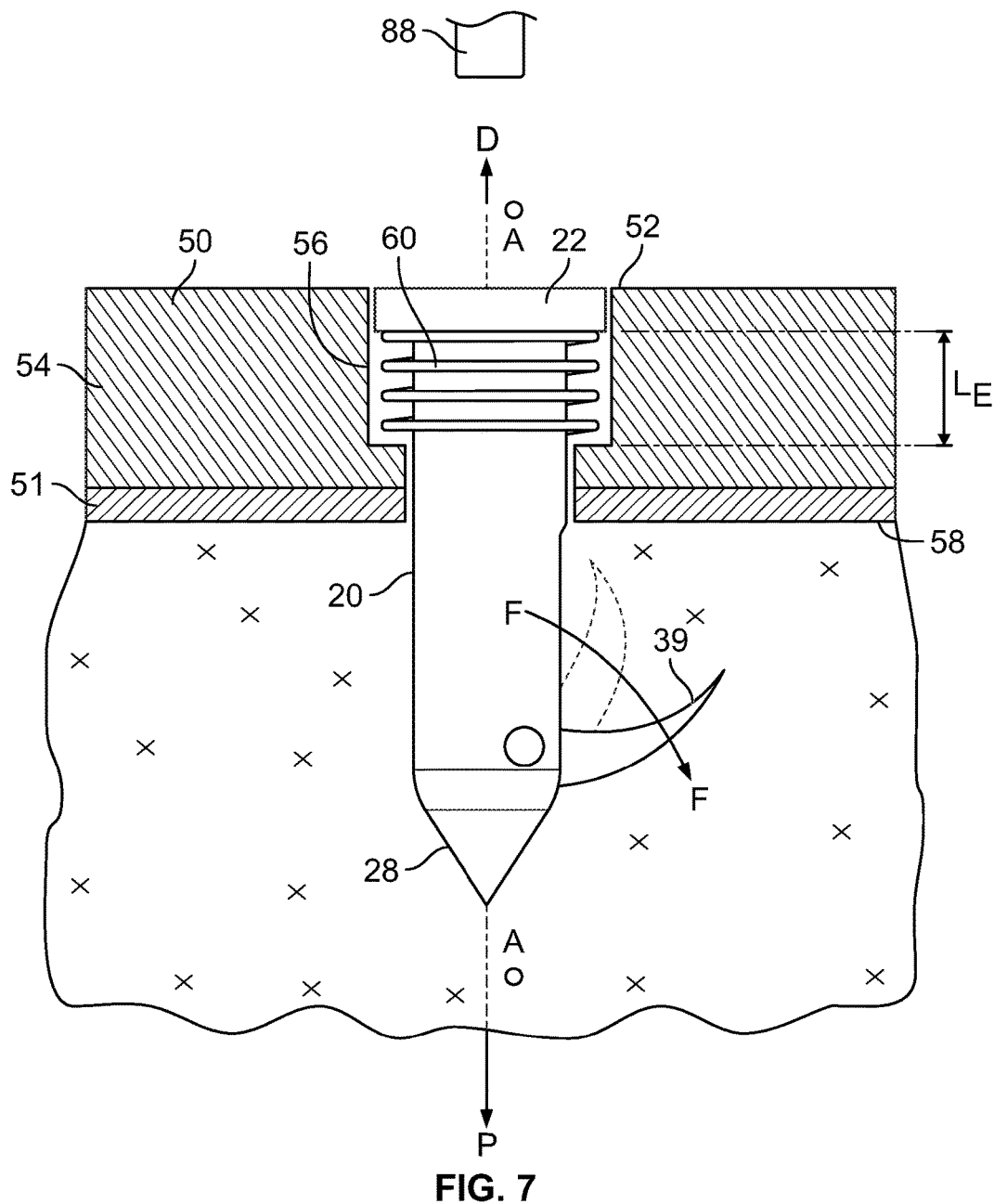

Proximal tip 28 of anchor 10 is adapted to penetrate living tissue 1, as shown in FIGS. 6-7. Tip 28 is conical with a smooth finish and preferably tapers from exterior surface 25 of body 20 towards anchor axis A-A to define a tissue penetrating point 29. Point 29 may be coaxial with axis A-A so as to penetrate a muscular portion of the human heart, such as the wall of the left ventricle, when a proximally-directed driving force is applied to anchor 10 along axis A-A. Pin hole 27 is adjacent tip 28 in FIGS. 1 and 3A so that a head portion of a pin 32 may sit firmly against body 20. Although not shown, pin hole 27 may have a countersunk portion adapted to receive a correspondingly shaped head portion of pin 32.

Figure 3B:
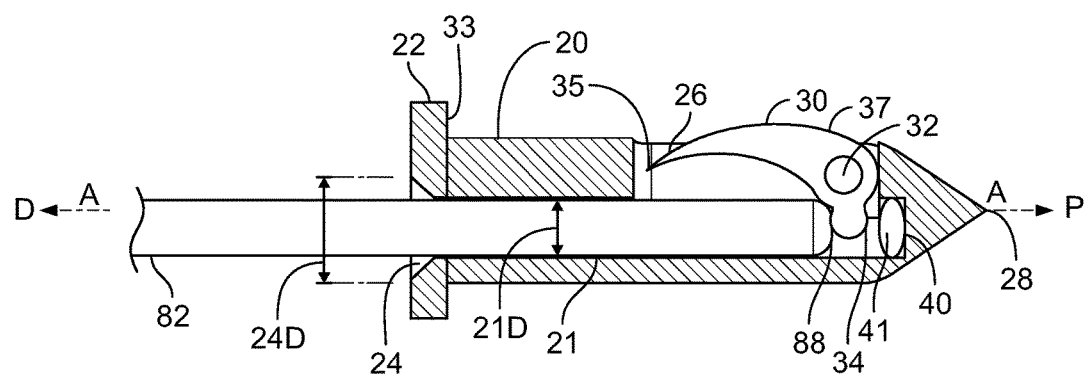
FIG. 3B is a side elevation sectional view of the tissue anchor shown in FIG. 1 with the barb in the retracted position.
Figure 4A:
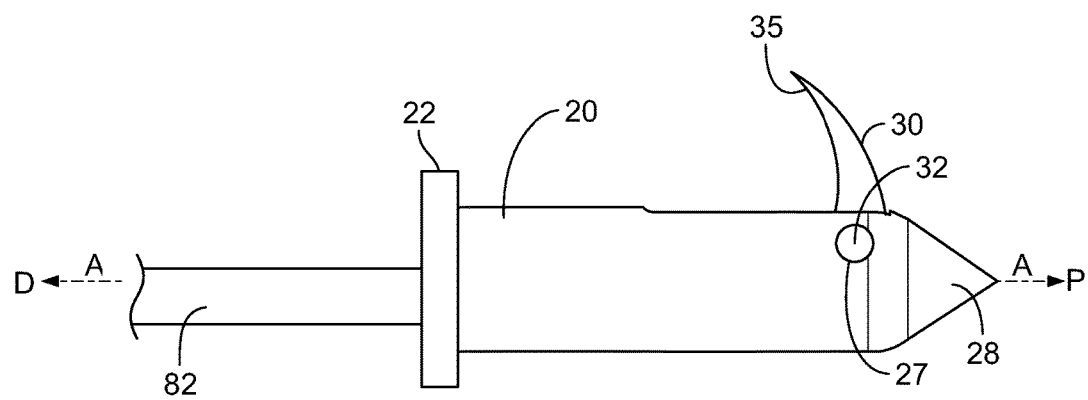
FIG. 4A is a side elevation view of the tissue anchor shown in FIG. 1 with the barb in the extended position.
Figure 4B:
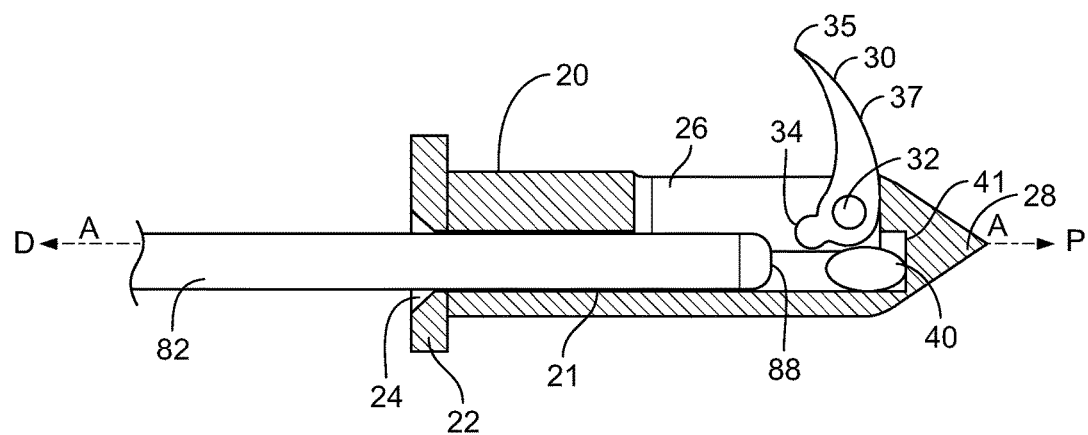
FIG. 4B is a side elevation sectional view of the tissue anchor shown in FIG. 1 with the barb in the extended position.

A barb 30 is preferably mounted to body 20 in barb opening 26 for movement between a retracted position, in which barb 30 is adjacent body 20 (FIGS. 3A-B); and an extended position, in which barb 30 projects outwardly from body 20 (FIGS. 4A-B). To facilitate these movements, barb 30 may have a pivot end 34 and a grip end 35. Barb 30 of FIGS. 3A-4B, for example, is mounted on body 20 by inserting pin 32, along axis P-P, through pin hole 27 and a corresponding pin hole 37 in pivot end 34. An end of pin 32 may be secured to body 20. For example, pin 32 may have a threaded end that is inserted into pin holes 27 and 37, and then engaged with a threaded hole (not shown) formed in body 20. Alternatively, pin 32 may be press-fit into a hole formed in body 20 or welded thereto.

The arrangement of pivot pin 32 and barb 30 allows a substantial portion of barb 30 to be disposed in opening 26 when it is moved in the retracted position (FIGS. 3A-B). When barb 30 is retracted, as in FIG. 3B, distal surface 39 may otherwise be described as an interior surface 39 of barb 30, while proximal surface 49 may otherwise be described as an exterior surface 49 of barb 30. In some embodiments, barb 30 may be rotated into opening 26 so that the entirety of exterior surface 49, including grip end 35, is tucked into opening 26. In other embodiments, only portions of exterior surface 49 of barb 30 may be rotated into opening 26. For example, in FIGS. 3A-B, grip end 35 and a substantial portion of barb 30, including all but a portion of exterior surface 49, are disposed in barb opening 26. Barb 30 preferably includes a barb width 30W (FIG. 1) that is sized to prevent surface 39 from cutting through tissue 1 when in the extended position (FIGS. 4A-B). By way of example, barb width 30W may be about 0.50 mm.

A first resilient element 40 is also contained in barb opening 26. As shown in FIGS. 3B and 4B, for example, element 40 is contained in internal cavity 41 of barb opening 26 so that a distal surface of resilient element 40 is adjacent a proximal surface of pivot end 34. A proximally-directed driving force may be applied by a portion of tool 70 to pivot end 34 so as to move barb 30 into the retracted position. Preferably, this driving force transforms resilient element 40 from an uncompressed state (FIG. 4B) to a compressed state (FIG. 3B), thereby moving barb 30 into the retracted position. First resilient element 40 is also positioned to bias barb 30 toward the extended position. For example, the resiliency of first element 40 allows it to store potential energy when compressed by pivot end 34. This potential energy is released when tool 70 is removed. Because the distal surface of first resilient element 40 is positioned adjacent the proximal surface of pivot end 34, this potential energy will be released as a distally-directed biasing force applied to pivot end 34 as element 40 expands from its compressed state (FIG. 3B) to its uncompressed state (FIG. 4B).

First resilient element 40 of FIGS. 3A-B is depicted as a hollow spherical element made of a silicone-based material, such as silicone rubber. Element 40 may be spherical or non-spherical, hollow or solid, silicone-based or otherwise depending upon the requisite biasing forces. Internal cavity 41 of opening 26 is depicted as having a rectangular profile adapted to contain element 40. Like element 40, internal cavity 41 may also assume any comparable profile shape, including any shape that corresponds with the shape of resilient element 40.

Figure 2:
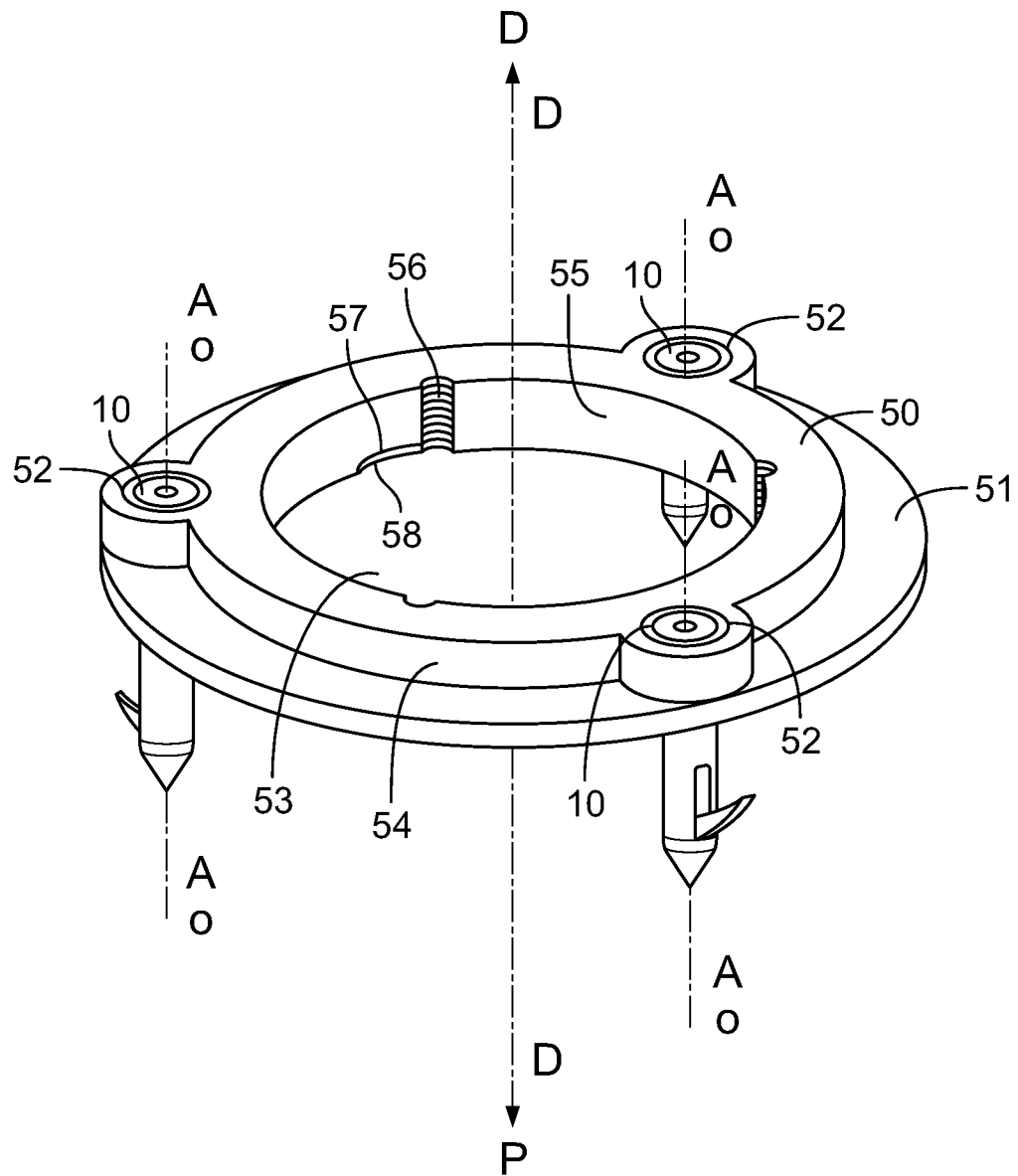
FIG. 2 is a front perspective view of an implantable device in accordance with another embodiment of the present invention.

An exemplary implantable device 50 is illustrated in FIGS. 2 and 6-7 as a mounting ring or plate. A device axis D-D extends longitudinally in a proximal-distal direction through device 50. Device 50 has a planar portion 51 with a central opening 53 and three anchor openings 52 extending therethrough. Central opening 53 is preferably coaxial with device axis D-D, whereas each anchor opening 52 extends along an anchor opening axis O-O that may be parallel or transverse with device axis D-D.

Each anchor opening 52 is adapted to receive an anchor 10 therein. Anchor opening 52, as shown in FIG. 6, has an inner or anchor opening diameter 52D that is larger than body diameter 20D, yet smaller than head diameter 22D. This difference allows body 20 to pass through an anchor opening 52 along anchor opening axis O-O when barb 30 is in the retracted position. For example, body 20 may be inserted into an anchor opening 52 along axis O-O until the proximal surface 33 of head 22 is adjacent device 50. A recess wall 54 preferably extends distally from planar portion 51 of device 50 to surround each anchor opening 52. In FIG. 6, each wall 54 defines a recess 56 that is coaxial with an anchor opening axis O-O. Each recess 56 is illustrated as having an inner or recess diameter 56D that is greater than head diameter 22D so that head 22 may be received therein.

Device 50 preferably has a second resilient element 60 mounted in each recess 56, as shown in FIGS. 6-7. Resilient element 60 is adapted to impart a distally-directed biasing force on the proximal surface 33 of anchor 10 so as to help move barb 30 into the extended position and sink barb 30 into living tissue 1. Each element 60 is depicted as a coil spring that is coaxial with an anchor opening axis O-O. As shown, second resilient element 60 desirably has a compressed length $L_C$ (FIG. 6), an equilibrium length $L_E$ (FIG. 7), and a travel length $L_T$ that is equal to its compressed length $L_C$ minus its equilibrium length $L_E$ when element 60 is unloaded. Element 60 may, when loaded, be at equilibrium length $L_E$ once anchor 10 has been sunk into tissue 1, as in FIG. 7. In some embodiments, the equilibrium length $L_E$ may be approximately equal to the height of recess wall 54 minus the height of head 22. Element 60 may be at its compressed length $L_C$ as anchor 10 is driven into an anchor opening 52. For example, each anchor 10 may be moved into an anchor opening 52 with barb 30 in the retracted position (FIG. 5), then advanced proximally until element 60 is compressed by proximal surface 33 of head 22 to its compressed length $L_C$ (FIG. 6).

Central opening 53 of FIG. 2 has a central opening diameter 53D that extends into device 50 to define an interior sidewall 55. As best shown in FIG. 2, a bayonet locking feature is formed on sidewall 55. The illustrated bayonet locking feature has three elements: a notch 56, a ramp 57, and a pit 58. Notch 56 extends proximally along sidewall 55 in a direction parallel to device axis D-D so as to intersect ramp 57. Ramp 57 extends into the proximal side of device 50 around a circumferential portion of central opening 53 between notch 56 and pit 58. In FIG. 2, pit 58 has a depth along device axis D-D that is less than the depth of adjacent portions of ramp 57. As explained below, notch 56 and ramp 57 guide a nub 79 on tool 70 through notch 56, around ramp 57, and into pit 58 so as secure device 50 to tool 70.

Figure 8:
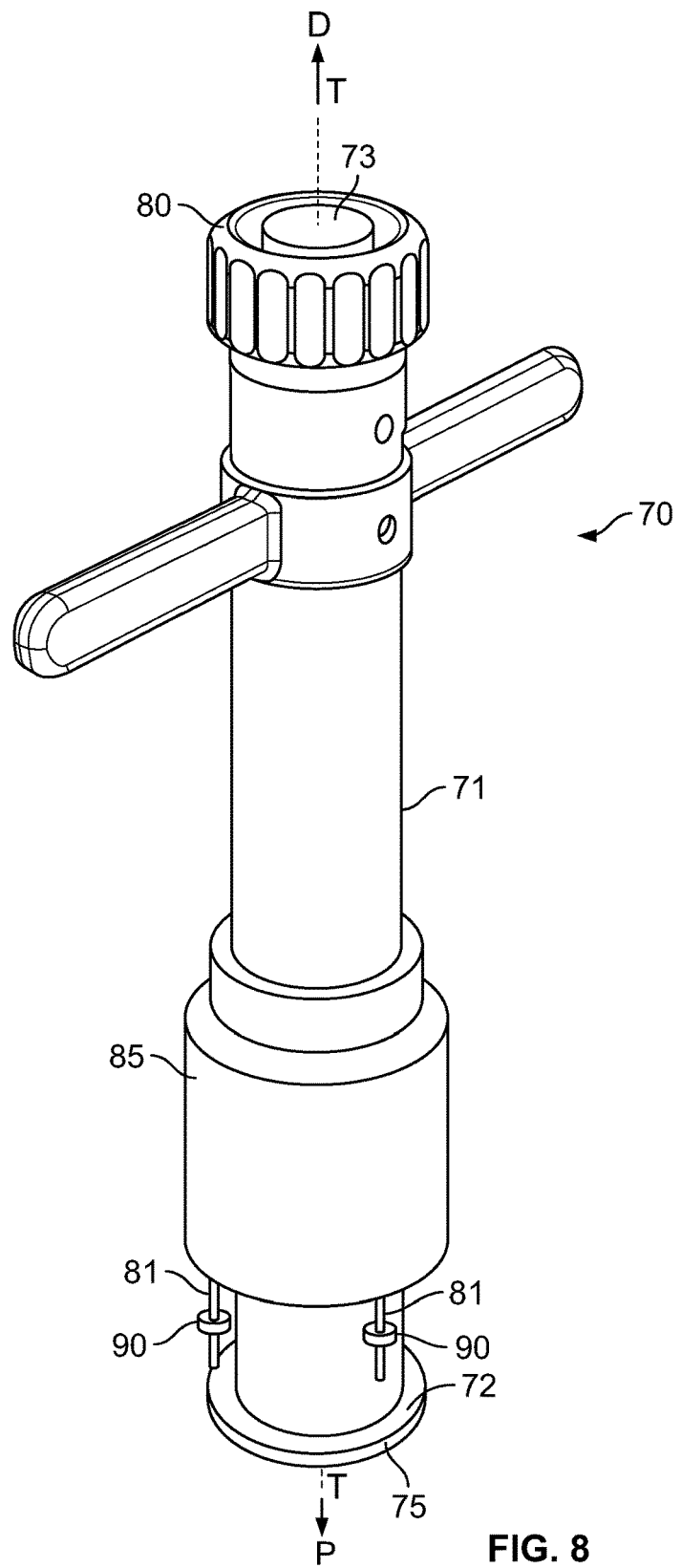
FIG. 8 is a front perspective view of a tool used with the implantable device and tissue anchors in accordance with another embodiment of the present invention.

A tool 70 (FIGS. 8-10B) may be used with device 50 and anchors 10. Tool 70 has a securing feature that is preferably adjacent the proximal end of tool 70 and an operating feature that is preferably adjacent the distal end of tool 70. These features work to implant or remove anchor 10 from tissue 1, preferably through one of the anchor openings 52 in device 50. As shown in FIG. 8, tool 70 has an elongated body 71 with a tool axis T-T. A lip 72 extends from body 71 in a direction transverse to tool axis T-T. Preferably, lip 72 has an outer or lip diameter 72D (FIG. 10A) that is larger than central opening diameter 53D.

Figure 9:
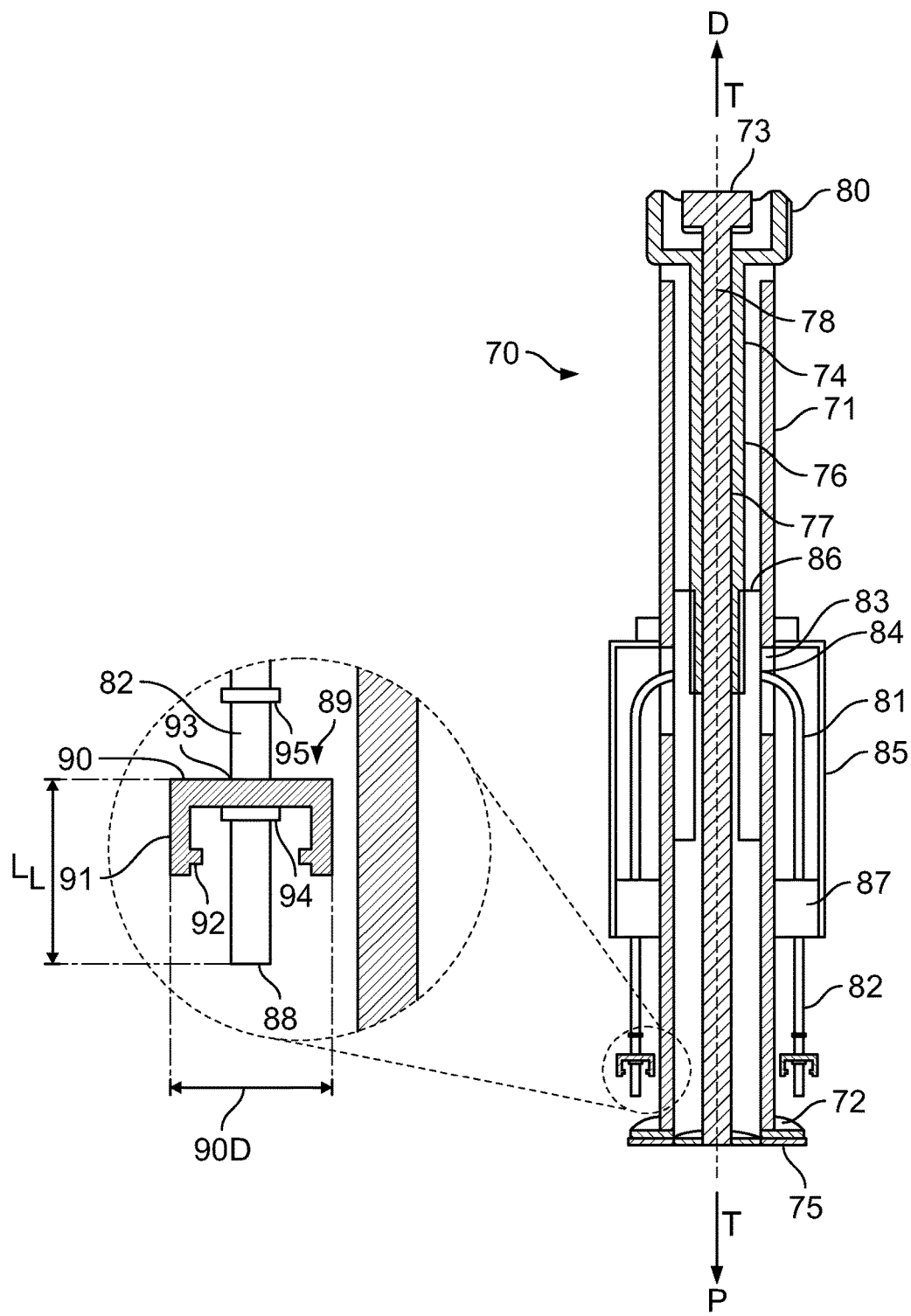
FIG. 9 is a front sectional view of the tool shown in FIG. 8.

The securing feature of tool 70 is utilized to removably attach device 50 to tool 70. This feature preferably includes an actuator that is operable to attach a portion of device 50 to tool 70. For example, in FIGS. 8-9, the actuator is a knob 80 with a knurled surface and an open internal cavity sized to receive a push button 73. A drive shaft 76 is attached to knob 80. Shaft 76 extends proximally from knob 80 to an internal point of a bore 74 extending through body 71. In FIG. 9, a bore 77 of shaft 76 is coaxial with bore 74. Bore 77 extends through shaft 76 along tool axis T-T and is adapted to receive a push rod 78 therein. Push rod 78 is attached to push button 73 at one end and a flange 75 at the other end. As shown, flange 75 has three nubs 79 extending from its outer perimeter. Each nub 79 is arranged in a pattern corresponding to the pattern of notches 56 (FIG. 2) described above with respect to central opening 53.

Figure 10B:
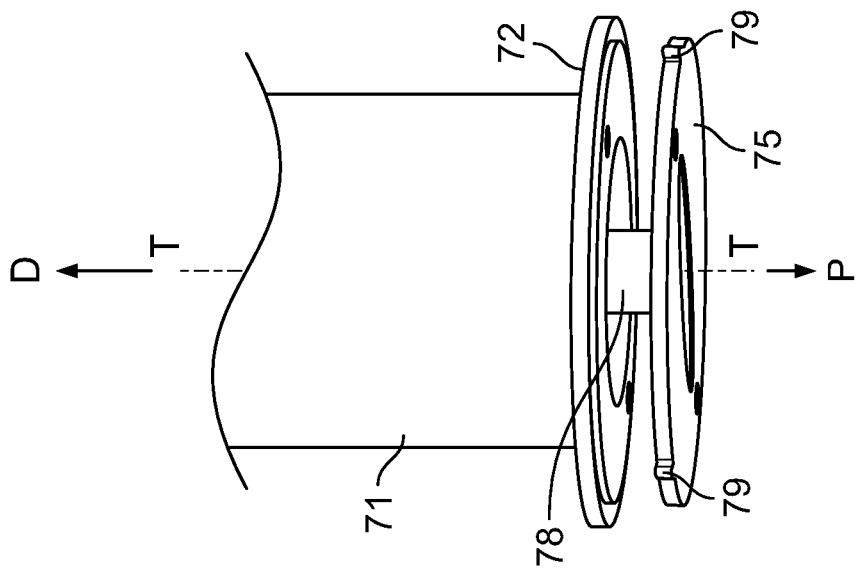
FIGS. 10A and 10B are front perspective views of the proximal end of the tool shown in FIG. 8.
Figure 10A:
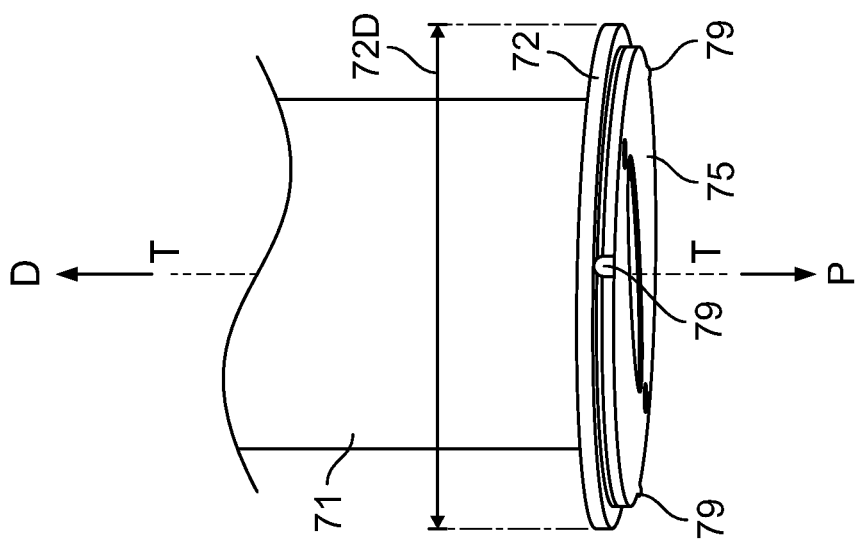

Push button 73 may be depressed along tool axis T-T so as to secure device 50 to tool 70. In this regard, push button 73 and push rod 78 are adapted to move between a first position, where the distal surface of flange 75 is adjacent a proximal surface of lip 72 (FIG. 10A); and a second position, where the distal surface of flange 75 is separated from the proximal surface of lip 72 (FIG. 10B). Merely by way of example, the axial movement of flange 75 between the first position and the second position may be about 7.0 mm. A third resilient element (not shown) may be positioned between button 73 and knob 80 so as to bias rod 78 and flange 75 towards the first position. Because of this third resilient element, device 50 may be secured to tool 70 by depressing button 73, guiding each nub 79 in a pit 58, and releasing button 73. A lock (not shown) may be provided for holding rod 78 and flange 75 in the first position.

The operating feature of tool 70 is utilized to drive anchor 10 into tissue 1. In FIG. 9, for example, this feature includes a plunger 86 that is threadably connected to the driveshaft 76 at an internal point within body 71. This connection allows plunger 86 to be configured for translational movement along tool axis T-T. For example, the threaded connection between plunger 86 and driveshaft 76 allows plunger 86 to be moved proximally along tool axis T-T by rotating knob 80 (and thus, driveshaft 76) about axis T-T in a first or driving direction. Conversely, plunger 86 may also be moved distally along tool axis T-T by rotating knob 80 in a second or non-driving direction.

Tool 70 of FIG. 9 has three driving rods 81 that are operably attached to plunger 86, one rod 81 for each anchor opening 52. Each rod 81 has a working end 82 opposite of a connecting end 84. The connecting end 84 of each rod 81 extends through a track 83 formed in body 71. Because of this connection, rotating knob 80 causes each rod 81 to be moved along tool axis T-T with attached plunger 86, independent of body 71. Each rod 81 is preferably a rigid element that extends out of track 83 and into an alignment feature 87 mounted on body 71. In FIG. 9, three alignment features 87 are provided, each being configured to guide one of the rods 81 towards an anchor opening 52. For example, alignment feature 87 may be a conduit that aligns the working end 82 of each rod 81 with anchor opening axis O-O. Alignment feature 87 thereby ensures that each anchor 10, when loaded onto a rod 81, will be moved into or out of an anchor opening 52 when knob 80 is rotated. A protective case 85 (FIG. 9) preferably surrounds the rods 81.

An exemplary working end 82 of each rod 81 is depicted in FIGS. 3B, 4B, and 9 as having a driving portion 88 and a gripping portion 89. Driving portion 88 is illustrated as a flat surface adapted to move barb 30 into the retracted position. As described above, driving portion 88 moves barb 30 by applying a proximally-directed driving force to pivot end 34.

Figure 5:
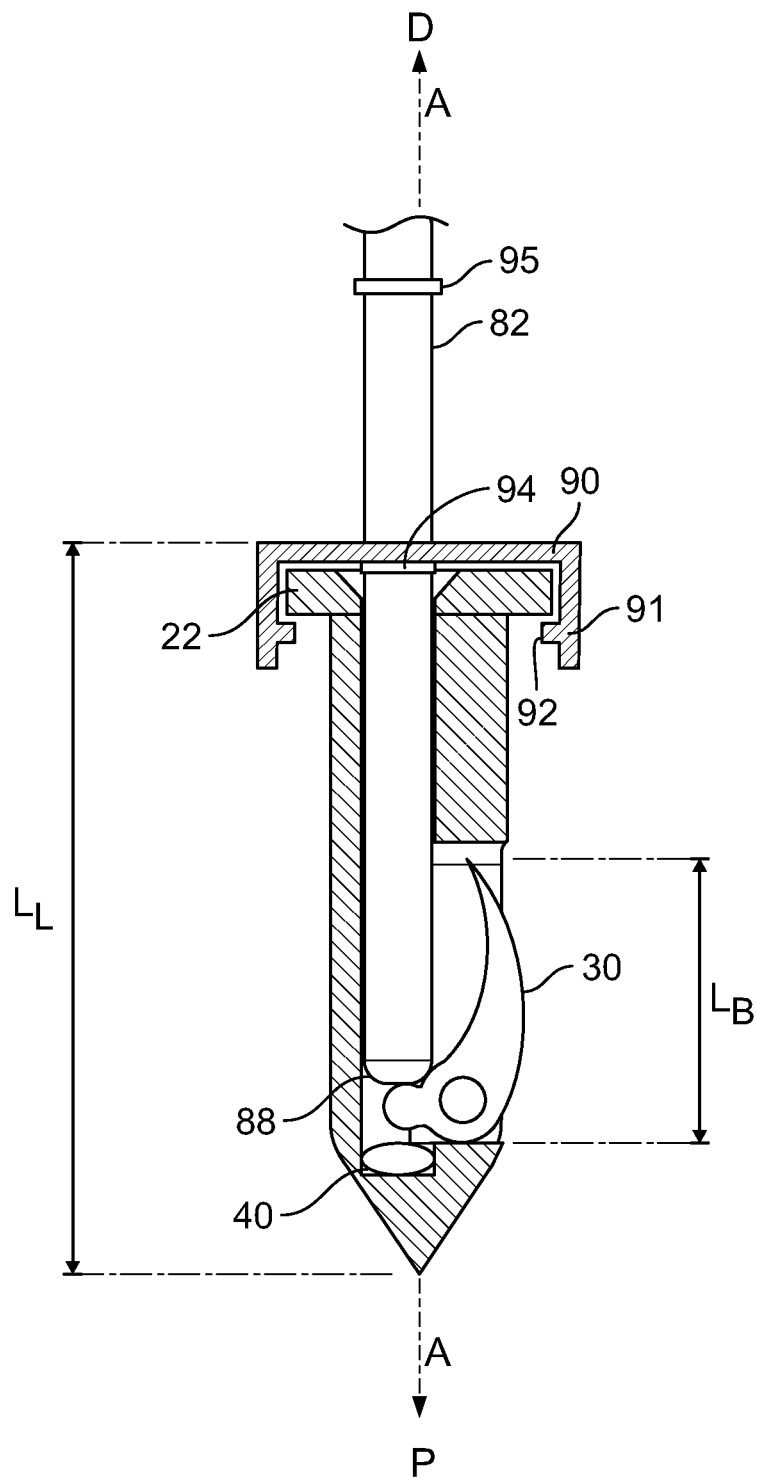
FIG. 5 is a front elevation sectional view of the tissue anchor shown in FIG. 1 with a cap.

An optional gripping portion 89 is illustrated in FIGS. 5, 6, and 9, as a cap 90. Each cap 90 may be removably attached to the head 22 of an anchor 10. For example, cap 90 is illustrated as having an outer or cap diameter 90D (FIG. 9) that is greater than anchor opening diameter 52D (FIG. 6). Cap 90 also has a peripheral sidewall 91 extending circumferentially around at least a portion of diameter 52D, and a protrusion 92 extending inwardly from sidewall 91 toward tool axis T-T. Protrusion 92 is preferably located at an interior point along the depth of sidewall 91 so that the entirety of head 22 may be captured in cap 90. Protrusion 92 allows the head 22 of each anchor 10 to be snapped into cap 90. In complement, protrusion 92 also ensures that barb 30 will be held in the retracted position once head 22 is snapped into cap 90. For example, in FIG. 5, barb 30 is held in the retracted position because the distally-directed biasing forces imposed by first resilient element 40, which would otherwise push anchor 10 away from cap 90, are offset by the holding forces imposed by protrusion 92.

To facilitate loading, cap 90 is illustrated as being slidably attached to working end 82. For example, as shown in FIGS. 5 and 9, cap 90 is depicted as having a central cap opening 93 sized to receive the driving portion 88 of a rod 81. Working end 82 has a proximal stop 94 opposite of a distal stop 95. Stops 94 and 95 allow cap 90 to slide along a defined portion of rod 81. Moreover, proximal stop 94 also ensures that cap 90 may be precisely spaced apart from driving portion 88 by a loading length $L_L$ (FIG. 9) so as to further ensure that barb 30 is held in the retracted position. Cap 90 may alternatively be fixed to a portion of working end 82 for this purpose.

Methods of using anchors 10 to secure device 50 to tissue 1 are also disclosed with reference to FIGS. 1-10B. As noted above, tool 70 may be used to drive each anchor 10 through an anchor opening 52. Therefore, an exemplary method of using anchor 10 may comprise the step of loading each anchor 10 into tool 70 so as to hold barb 30 in the retracted position, as illustrated in FIG. 5. This loading step may comprise inserting the driving portion 88 of tool 70 into bore opening 24 of head 22 until the proximal surface of portion 88 contacts the distal surface of pivot end 34. Once positioned, driving portion 88 may then be advanced proximally until pivot end 34 compresses first resilient element 40, thereby moving barb 30 into the retracted position. Protrusion 92 of cap 90 may then be positioned under the proximal surface of head 22 so as to load anchor 10 by retaining head 22 in cap 90 and barb 30 within opening 26.

This exemplary method further comprises securing device 50 to tool 70. For example, device 50 may be secured to tool 70 by moving push button 73 into the second position so as to separate flange 75 from lip 72 (FIG. 10B), guiding nubs 79 into pit 58 via notch 56 and ramp 57, and then moving button 73 into the first position to as capture a central portion of device 50 between flange 75 and lip 72. If push button 73 is biased towards the first position by a third resilient element (not shown), then button 73 may simply be released so that biasing forces imparted by the third resilient may be used to move flange 75.

The loading and securing steps described above may be completed in any order. Either way, once both of those steps are completed, then each anchor 10 is ready for insertion into one of the anchor openings 52. Preferably, because of alignment feature 87, tool axis T-T is coaxial with device axis D-D and anchor axis A-A is coaxial with each anchor opening axis O-O once the loading and securing steps are complete.

Tool 70 may be utilized to place implantable device 50 adjacent tissue 1 (FIG. 6), preferably after anchors 10 have been loaded onto tool 70 and device 50 attached thereto. For example, if tissue 1 is a heart, then this method may comprise placing a tissue contacting surface 58 of device 50 adjacent the apex of a heart so that each anchor opening 52 opens towards the wall of the left ventricle. Once device 50 is positioned, this step may further comprise driving tissue anchors 10 into living tissue 1 through openings 52. For example, knob 80 may be rotated in the driving direction to move each anchor 10 proximally along the anchor opening axis O-O until the proximal tip 28 of the anchor 10 has been driven into tissue 1 through an anchor opening 52. In some embodiments, anchor 10 may be moved proximally until the second resilient element 60 has been compressed by surface 33 of head 22 from its equilibrium length $L_E$ (FIG. 7) to its compressed length $L_C$ (FIG. 6).

Because cap diameter 90D is greater than anchor opening diameter 52D, head 22 will automatically detach from cap 90 as anchors 10 are driven through openings 52. For example, a proximal surface of each cap 90 will contact a distal surface of device 50 once knob 80 has been rotated a first number of turns. Rotating knob 80 a second number of turns will thus cause sidewall 91 of cap 90 to flex away from combined axes A-A and O-O as anchor 10 is driven into opening 52. This flexure causes protrusion 92 of cap 90 to move away from proximal surface 33 of head 22, thereby detaching anchor 10 from cap 90. The driving forces applied by tool 70 to anchor 10 are proximally-directed, whereas the biasing forces applied by second resilient element to anchor 10 are distally-directed. Therefore, driving portion 88 of tool 70 will remain in contact with pivot end 34 of barb 30 even after head 22 has been detached from cap 90.

This exemplary method may further comprise rotating knob 22 in the non-driving direction so as to move barb 30 into the extended position and sink barb 30 into tissue 1. The configuration of first and second resilient elements 40 and 60 permits this motion. For example, as noted above, first resilient element 40 (FIGS. 3B and 4B) is adapted to impart a distally-directed biasing force onto the proximal surface of pivot end 34. This biasing force moves barb 30 into the extended position after anchor 10 has been driven into tissue 1. As shown by leader line F-F in FIG. 7, for example, the biasing forces imparted by element 40 will move grip end 35 of barb 30 at least partially out of opening 26 as driving portion 88 is moved distally away from pivot end 34. Once barb 30 has been so moved, then grip end 35 may grip a portion of tissue 1.

The distally-directed biasing forces imparted by second resilient element 60 may help to fully move barb 30 out of opening 26. For example, the distally-directed biasing forces imparted onto proximal surface 33 of head 22 by element 60 will pull anchor 10 distally along the combined axes A-A and O-O towards device 50. If grip end 35 has gripped some portion of tissue 1 (FIG. 7), then the distally-directed biasing force applied by second resilient element 60 will also help to pull barb 30 out of opening 26. Preferably, barb 30 is fully extended after element 60 has been moved along a first portion of travel length $L_T$.

The distally-directed biasing forces imparted by element 60 may also be used to sink barb 30 into tissue 1. For example, once barb 30 has been fully extended, then any distally-directed biasing forces applied by element 60 will be opposed by a proximally-directed set of reaction forces applied by tissue 1. Barb 30 will thus continue moving distally away from device 50 until the biasing forces of element 60 are in equilibrium with the reaction forces of tissue 1, at which point barb 30 has been sunk into tissue 1. Second resilient element 60 will assume its equilibrium length $L_E$ once these forces are in equilibrium. Preferably, barb 30 is sunk into tissue 1 after element 60 has moved along a second portion of its travel length $L_T$ to assume its equilibrium length $L_E$. The dimensions of barb 30 relative to element 60 promote this motion. For example, barb 30 may have a barb length $L_B$ along anchor axis A-A (FIG. 5) that is longer than the travel length $L_T$ of second resilient element 60 along anchor opening axis O-O (defined above). In some embodiments, travel length $L_T$ may be equal to about two thirds of barb length $L_B$.

With this method, device 50 may desirably be secured to tissue 1 without application of any substantial driving forces along tool axis T-T. Instead, because all of the rotational forces applied to knob 73 about tool axis T-T are converted by shaft 76 and plunger 86 into translational forces along axis T-T, the operator may simply place device 50 adjacent the tissue 1 and then rotate knob 73 until barb 30 has been sunk into tissue 1. Accordingly, this method will dramatically reduce the likelihood that the tissue 1 will be damaged, especially if tissue 1 is a hollow organ like the heart.

Tool 70 may also be used to remove anchors 10 and device 50 from tissue 1 without damaging tissue 1. An exemplary removal method may comprise securing device 50 to tool 70 in the manner set for above. This securing step ensures that living tissue 1 will not be crushed by any of the proximally-directed forces applied to anchor 10 by tool 70. Each driving portion 88 of tool 70 is preferably parallel with anchor axis A-A and anchor opening axis O-O once device 50 is secured to tool 70. Therefore, this exemplary method may further comprise the step of rotating knob 73 a first number of turns in the driving direction until driving portion 88 contacts pivot end 34.

Barb 30 may need to be unsunk before it can be moved to the retracted position. The travel length $L_T$ of second resilient element 60 also allows barb 30 be unsunk as it is moved into the retracted position. For example, knob 73 may be rotated a second number of turns in the driving direction so as to both compress second resilient element 60 and move barb 30 into the retracted position. This, preferably simultaneous, movement ensures that distal surface 39 of extend barb 30 (FIG. 1) will be moved away from tissue 1 as barb 30 is moved into the retracted position, thereby allowing barb 30 to be rotated into barb opening 26 without pinching or cutting a portion of tissue 1. In some embodiments, element 60 is moved entirely from its equilibrium length $L_E$ to its compressed length $L_C$ as barb 30 is rotated.

Device 50 may be removed from its position adjacent living tissue 1 once each barb 30 has been moved into the retracted position. For example, driving portion 88 of tool 70 may be utilized to apply a proximally-directed driving force that both compresses element 60 and moves barb into the retracted position. In addition to moving barb 30, this driving force will also pin each anchor 10 inside one of the anchor openings 52 once second resilient element 60 has obtained its compressed length $L_C$. Accordingly, each anchor 10 may be removed together with device 50 once each of the barbs 30 has been retracted.

Many features of the embodiments described above can be varied without departing from the present invention. Some of these varied embodiments are described separately below. Of course, any feature described below with respect to these alternative embodiments may also be incorporated into any embodiment described above.

Distal head 22 is described has having a bore opening 24 that extends through distal head 22 to be in communication with bore 21. Bore 21 is depicted as being parallel to and yet offset from anchor axis A-A. Alternatively, bore 21 may be coaxial with anchor axis A-A. Each of head 22, opening 24 and bore 21 are depicted as having a circular cross-section. This is not required as any of these elements might alternatively have another cross-sectional shape. For example, head 22 may have a hexagonal cross-section that is engageable with a correspondingly hexagonal shaped embodiment of cap 90. As further example, each opening 24 may also have a cross-sectional shape that is keyed to receive a correspondingly shaped driving portion 88 at a particular orientation with respect to anchor axis A-A.

Elements of anchor 10 are described as having a smooth finish, such as body 20. This type of surface treatment ensures that those elements of anchor 10 will pass smoothly through any embodiment of anchor opening 52. Any portion of anchor 10 may have an alternative surface treatment. For example, the exterior surface of body 20 or tip 28 may alternatively have one or more muscle securing elements attached thereto. In some embodiments, these securing elements may be embodied as a thread that runs around a portion of body 20 so that anchor 10 may be screwed into tissue 1 before barb 30 is moved into the extended position. Tool 70 may be modified to facilitate this screwing motion. For example, alignment feature 87 of tool 70 might have a gearbox that allows each rod 81 to be rotated as it is moved along anchor opening axis O-O. In other embodiments, these securement elements may be grooves, nubs, ridges, or other protrusions extending away from or towards body 20. Anchor opening 52 may be further enlarged or cut-out to permit receipt or removal of any of these alternative embodiments of body 20.

Each anchor 10 is depicted as having a single body 20. Anchor 10 may alternatively be embodied as a staple having at least two bodies 20 joined by a center section, wherein each body has a barb 30 in accordance with the present invention. Any number of bodies 30 may be combined to form a staple. Elements of device 50 may be modified to accommodate these alternative embodiments of anchor 10. For example, device 50 may have a pair of openings 52 that are adjacent one another and surrounded by a common recess 56 that has been sized to receive the center section of the staple. Elements of tool 70 may be similarly modified. For example, tool 70 may have a gripping portion 89 that is engageable with the center section of anchor 10 and a plurality of rods 81, wherein each rod 81 is configured to simultaneously engage one of the barbs 30.

Barb 30 is depicted in FIG. 1 as being smoothly curved along its length. Alternatively, barb 30 may be bent at some point along its length to have an abrupt hook shape. Alternatively still, either a portion of grip end 35 or a proximal surface of barb 30, when extended, may have one or more tissue gripping elements that are adapted to move barb 30 into the extended position. For example, grip end 35 may have ridges or other tissue-catching protrusions on said proximal surface to help pull barb 30 out of opening 26 when the proximally-directed driving force applied by driving portion 88 is released. To provide an additional means for gripping living tissue 1, barb width 30W may also be varied along barb length $L_B$. For example, barb 30 may have a bulbous shape with a first barb width 30W at pivot end 34 that is smaller than a second barb width 30W adjacent grip end 35, thereby increasing the surface area of distal surface 39 (FIG. 1).

Barb 30 may comprise a plurality of barbs 30. Each of the plurality of barbs 30 is preferably mounted to body 20 adjacent the proximal tip 28 for movement between their respective retracted and extended positions. In some embodiments, at least two barbs 30 are mounted on body 20 in opposite directions. For example, body 20 may have a first opening 26, as shown in FIG. 1, and a second opening (not shown) on the opposite side of body 20 that is otherwise identical to opening 26. This configuration allows the at least two barbs 30 to be mounted on a single pin 32. In other embodiments, pin 32 and pin hole 27 are modified to accommodate a plurality of barbs 30. For example, an additional pivot pin 32 may be utilized for each barb 30, wherein each pin 32 is attached to body 20 via a separate hole 27. Alternatively, each pivot pin 32 may be embodied as a protrusion, such as a cylindrical bar, that extends outward from the interior surface of body 20 to engage the pivot end 34 of each barb 30 at various points along anchor axis A-A.

The spherical shape of first resilient element 40 permits interaction with a plurality of pivot ends 34. Nonetheless, each pivot end 34 may be adapted to engage an alternative embodiment of first resilient element 40. For example, element 40 may alternatively comprise a spring that is mounted below pivot end 34 of barb 30 so as to impart the distally-directed biasing forces described above. If multiple pivot ends 34 are to engage element 40, then a plate element may be inserted between the pivot ends 34 and any embodiment of first resilient element 40 to evenly distribute any forces applied thereby. In still other embodiments, first resilient element 40 may comprise a resilient band that is mounted inside of internal cavity 41. This band may, for example, be adapted to span between pivot end 34 and a protrusion, such as a hook, extending outward from an internal surface of body 20 so as to bias barb 30 towards the extended position.

Retractable barb 30 has been described as an element that rotates into or out of opening 26. Other forms of movement are also contemplated. For example, a barb 30 may alternatively be embodied as a securement element that is moved along a substantially linear axis. In this alternative embodiment, the securement element may, for example, a triangular shaped element that is mounted on a track within body 20. First element 40 may then be positioned between body 20 and barb 30 so as to bias the securement element into a retracted position. Driving portion 88 of tool 70 may then be inserted into bore 21 so as to move the securement element into the retracted position by, for example, wedging between the securement element and first element 40.

Second resilient element 60 has been described as a coil spring that is coaxial with anchor opening axis O-O. Element 60 may be embodied as any resilient element adapted to apply the biasing forces described herein. For example, second resilient element 60 may alternatively be an annular coil spring that encircles a portion of tissue anchor 10 about its proximal-distal axis. To achieve the requisite travel length $L_T$, each winding of said spring may deflect, as needed, to facilitate implantation or removal of anchor 10 in the manner described above. Alternatively still, second resilient element 60 may comprise a toroidal element, such as a compressible disc or a hollow ring. This allows element 60 to also serve as sealing element that either prevents bodily fluids from entering anchor opening 52 after anchor 10 has been inserted therein or acts to further dampen the movements of anchor 10. Of course, element 60 might also be assembled from a combination of such elements.

Device 50 has been described has having a recess 56 that is adapted to house second resilient element 60. A portion of recess wall 54 may be offset from recess diameter 56D so as to retain element 60 in recess 56. Element 60 may also be affixed to device 50 by other means, such as adhesive or welding. Any embodiment of second resilient element 60 may also be mounted on anchor 10 so that anchor 10 and resilient element 60 can be inserted into opening 52 as a tissue anchor assembly. The elongated body 20 of anchor 10 may, for example, have a protrusion for securing element 60 thereto. Alternatively, a portion of element 60 may be welded or otherwise affixed to proximal surface 33 of head 22.

Device 50 has been also described as a mounting ring having three anchor openings 52. Of course, device 50 may be any implantable device, having any number of anchor openings 52. The relative size of each anchor 10 and corresponding anchor opening 52 are described in similar terms; however, the size of each anchor and anchor opening may vary. Device 50 is also described as having a tissue contacting surface 58 that is directly mounted to tissue 1. Of course, the length of anchor 20 may be modified so that another implantable device, such as a gasket, seal, or other device, is mounted between tissue 1 and surface 58.

An exemplary bayonet locking feature is described above with reference to the central opening 53. Any known locking feature may alternatively be employed. For example, notch 56 may be embodied as a lug formed into sidewall 55 of central opening 53, or other equivalent structure.

Alternative embodiments of tool 70 are also contemplated. The securing feature of tool 70, for example, is described has having a set of nubs 79 that are arranged in a pattern corresponding to the pattern of notches 56 in device 50. Nubs 79 may, of course, be modified to operate with alternative embodiments of notch 56, such as the aforementioned lugs. The operating feature of tool 70 may also be modified. For example, plunger 86 is described as being threadably connected to shaft 72. This connection may incorporate threads with a uniform pitch, wherein every turn of knob 80 moves plunger 86 about the same length along tool axis T-T. Alternatively, the threaded connection between plunger 86 and shaft 72 may incorporate threads with a variable pitch. For example, a first set of threads having a first thread pitch may be utilized to move anchor 10 towards tissue 1 in rapid fashion when anchor 10 is remote from tissue 1, whereas a second set of threads having a second thread pitch are utilized to move anchor 10 towards tissue 1 at a slower pace when anchor 10 is adjacent tissue 1.

Tool 70 is described has having one driving rod 81 for each anchor opening 52 so that all of the anchors 10 can be implanted at once. The ability to implant multiple anchors is desirable; however, it is not necessary. For example, in an alternative embodiment of tool 70, a single rod 81 may be operably attached to body 71. In this alternative embodiment, alignment feature 87 of tool 70 may have a gearbox that allows the single rod 81 to be rotated about tool axis T-T so that an anchor 10 may be inserted into an anchor opening 52 located at any point on device 50. Alternatively still, the entirety of tool 70 may be embodied as a single rod with equivalent driving and gripping portions 88 and 89, each portion being adapted to remove an anchor 10 independently from device 50.

Gripping portion 89 is described as a cap 90 that snaps over the top of head 22. This is an optional feature. For example, each anchor 10 may be placed into an anchor opening 52 to form a device assembly, wherein the travel length $L_T$ of second resilient element 60 ensures that barb 30 will remain in the retracted position. Once this device assembly has been formed, then a driving portion 88 may then be advanced to secure each anchor 10 in an opening 52 with barb 30 in the retracted position. In this regard, the methods described above may be similarly executed without reference to optional cap 90. Gripping portion 89 may alternatively be any element capable of attachment with head 22 of anchor 10, such as jaws, grippers, magnetic couplers, or the like. Any embodiment of gripping portion 89 may be passively attached to head 22, like cap 90, or operably attached to head 22. For example, portion 89 may be set of jaws that are adapted to grip a portion of head 22. Each jaw of portion 89 may, as further example, be operable via a set of actuating cables that are mounted on or inside of each rod 81 and operably attached to the operating portion of tool 70.

Although the present invention has been described with reference to particular embodiments, it is to be understood that these embodiments are merely illustrative of the principles and applications described herein. It is therefore to be understood that numerous modifications may be made to each embodiments and that other arrangements may be devised without departing from the spirit and scope of the present invention as defined by the appended claims.

The invention claimed is:

1. A tissue anchor comprising:
    an elongated body having a proximal end defining a tip, and a distal end;
    a barb having a pivot end, the barb being mounted to the elongated body adjacent the proximal end for movement between a retracted position and an extended position in which the barb projects outwardly from the elongated body; and
    a first resilient element disposed between the tip of the elongated body and the pivot end of the barb, the first resilient element including a compressed state when the barb is in the retracted position, the compressed state including the first resilient element being compressed toward the proximal end of the body from a first diameter to a second diameter smaller than the first diameter wherein the barb is movable into the retracted position through the application of a force to the pivot end, thereby compressing the first resilient element, and wherein the elongated body has a bore extending from the pivot end to an opening in the distal end, the bore being sized to receive a tool adapted to apply the force to the pivot end through the bore.

2. The tissue anchor of claim 1, wherein the proximal end has a tissue penetrating tip.

3. The tissue anchor of claim 1, wherein the elongated body has an opening adjacent the proximal end and a pivot end of the barb is pivotally mounted to the body within the opening.

4. The tissue anchor of claim 3, wherein the entire barb is disposed through the opening and within the elongated body when in the retracted position.

5. The tissue anchor of claim 4, wherein the first resilient element is connected between the elongated body and the barb to bias the barb toward the extended position.

6. The tissue anchor of claim 5, wherein the first resilient element is housed within the elongated body proximal to the pivot end of the barb.

7. A method of anchoring an implantable device to a living tissue using the tissue anchor of claim 1, comprising the steps of:

placing a proximal surface of the implantable device adjacent the living tissue;

driving the tip of the tissue anchor into the living tissue through an opening in the implantable device; and moving the barb into the extended position so as to grip the living tissue and hold the proximal surface of the implantable device adjacent the living tissue.

8. The method of claim 7, further comprising a step of compressing a second resilient element seated between a distal end of the tissue anchor and a surface of the implantable device as the barb is moved into the extended position.

9. The method of claim 8, further comprising a step of decompressing the second resilient element so as to sink the barb into the living tissue.

10. A method of removing an implantable device and the tissue anchor of claim 1 from a living tissue, comprising the steps of:

holding the implantable device in a fixed position relative to the living tissue;

moving the barb into the retracted position; and removing the tissue anchor and the device from the living tissue.

\* \* \* \* \*